(12) United States Patent
Wojciechowski et al.

(10) Patent No.: US 10,596,062 B2
(45) Date of Patent: Mar. 24, 2020

(54) VISUAL REHABILITATION SYSTEMS AND METHODS

(71) Applicant: MAGNO PROCESSING SYSTEMS, INC., Clackamas, OR (US)

(72) Inventors: Bruce Wojciechowski, Clackamas, OR (US); Jeanie Schwenk, Hillsboro, OR (US)

(73) Assignee: MAGNO PROCESSING SYSTEMS, INC., Clackamas, OR (US)

(*) Notice: Subject to any disclaimer, the term of this patent is extended or adjusted under 35 U.S.C. 154(b) by 0 days.

(21) Appl. No.: 15/915,906

(22) Filed: Mar. 8, 2018

(65) Prior Publication Data

US 2018/0193218 A1   Jul. 12, 2018

Related U.S. Application Data

(63) Continuation of application No. 15/012,129, filed on Feb. 1, 2016, now Pat. No. 9,931,266.

(60) Provisional application No. 62/110,150, filed on Jan. 30, 2015.

(51) Int. Cl.
*A61B 3/00* (2006.01)
*A61H 5/00* (2006.01)
*A61B 3/10* (2006.01)

(52) U.S. Cl.
CPC .............. *A61H 5/00* (2013.01); *A61B 3/10* (2013.01); *A61H 2201/1604* (2013.01); *A61H 2201/165* (2013.01); *A61H 2201/5012* (2013.01); *A61H 2201/5038* (2013.01)

(58) Field of Classification Search
CPC .......... A61H 5/00; A61B 3/032; A61B 3/024; A61B 3/0033; A61B 3/08

USPC ........................................................ 351/203
See application file for complete search history.

(56) References Cited

U.S. PATENT DOCUMENTS

| | | |
|---|---|---|
| 5,394,517 A | 2/1995 | Kalawsky |
| 5,777,715 A | 7/1998 | Kruegle et al. |
| 6,077,237 A | 6/2000 | Campbell et al. |
| 6,301,050 B1 | 10/2001 | Deleon |
| 6,463,328 B1 | 10/2002 | John |
| 6,464,356 B1 | 10/2002 | Sabel |
| 6,990,377 B2 | 1/2006 | Gliner et al. |
| 7,753,524 B2 | 7/2010 | Sabel |
| 7,988,287 B1 | 8/2011 | Butler |
| 8,602,555 B2 | 12/2013 | Backus et al. |

(Continued)

FOREIGN PATENT DOCUMENTS

| | | |
|---|---|---|
| FR | 2668370 A1 | 4/1992 |
| WO | 2011089296 A1 | 7/2011 |

OTHER PUBLICATIONS

Capelle, "A Real-Time Experimental Prototype for Enhancement of Vision Rehabilitation Using Auditory Substitution", IEEE Transactions on Biomedical Engineering, v. 45, No. 10, pp. 1279-1293, dated Oct. 1998.

(Continued)

*Primary Examiner* — Mohammed A Hasan
(74) *Attorney, Agent, or Firm* — Miller Nash Graham & Dunn LLP

(57) ABSTRACT

The system can include a display device, a processor, and a computer readable medium having instructions for a visual rehabilitation program to perform a visual rehabilitation method including causing the display device to visually present to a user one or more images.

19 Claims, 16 Drawing Sheets

(56) References Cited

U.S. PATENT DOCUMENTS

| | | | |
|---|---|---|---|
| 8,788,197 B2 | 7/2014 | Fink | |
| 8,820,930 B2 * | 9/2014 | Fateh | |
| 9,931,266 B2 * | 4/2018 | Wojciechowski | ....... A61H 5/00 |
| 2009/0009714 A1 * | 1/2009 | Clarke | ................... A61B 3/005 |
| | | | 351/203 |
| 2010/0280372 A1 | 11/2010 | Poolman | |
| 2010/0283969 A1 | 11/2010 | Cooperstock et al. | |
| 2011/0004126 A1 | 1/2011 | Einav et al. | |
| 2011/0118806 A1 | 5/2011 | Pascual-Leone et al. | |
| 2012/0108909 A1 | 5/2012 | Slolbounov | |
| 2013/0012832 A1 | 1/2013 | Zelinsky | |
| 2013/0131985 A1 | 5/2013 | Weiland | |
| 2013/0281759 A1 | 10/2013 | Hagedorn et al. | |
| 2013/0314669 A1 | 11/2013 | Levin | |
| 2014/0249454 A1 | 9/2014 | Carpentier | |
| 2015/0150444 A1 | 6/2015 | Bex et al. | |
| 2016/0220439 A1 | 8/2016 | Wojciechowski | |
| 2017/0156965 A1 * | 6/2017 | Geisinger | .............. G16H 50/20 |

OTHER PUBLICATIONS

Yamamoto et al., "Analysis of Brain Activation by Visually and Auditory Stimulation After Visually and Auditory Simultaneous Stimulation Using f-MRI", Annual International Conference of the IEEE Engineering in Medical and Biology, v. 26, pp. 1872-1874, 2004.

Massof et al., "Low-Vision Enhancement System", 1994 SID International Symposium Digest of Technical Papers, Jun. 1994.

Bergsma et al., "Transfer Effects of Training-Induced Visual Field Recovery in Chronic Stroke Patients", Ultrecht University, Faculty of Science, Dept. of Functional Neurobiology, via Google Scholar.

* cited by examiner

VISUAL REHABILITATION SYSTEMS AND METHODS

CROSS-REFERENCE TO RELATED APPLICATION

This application is a continuation of U.S. Non-Provisional patent application Ser. No. 15/012,129, titled "Visual Rehabilitation Systems and Methods" and filed on Feb. 1, 2016, which claims the benefit of U.S. Provisional Patent Application Ser. No. 62/110,150, titled "Visual Rehabilitation Systems and Methods" and filed on Jan. 30, 2015, the content of which is fully incorporated by reference herein.

BACKGROUND

In the United States, an estimated 1.5 million people sustain a traumatic brain injury annually. Such traumatic brain injuries are incurred in a number of manners, such as through falls, vehicle accidents, violence, sport injuries, explosive blasts and combat injuries. People with traumatic brain injuries suffer from wide-ranging physical and psychological effects that may appear immediately after the injury or even appear much later. Symptoms include but are not limited to loss of consciousness, altered states of consciousness, headache, nausea or vomiting, fatigue or drowsiness, changes in sleeping patterns, loss of balance, dizziness, and vision changes. The quality of life of traumatic brain injury patients may be significantly impacted through such debilitating symptoms.

One of the fundamental processes with which people interact with the world is through the visual system. The visual system is one of the main areas that are affected by a traumatic brain injury. The loss or even a small impairment of a patient's visual system can mean day-to-day activities, such as cooking, reading, bathing, buying groceries, become difficult or impossible to complete. Further, when a visual system has been damaged, it impacts all systems and the deficits are devastating as vision is the process of deriving meaning from what is seen. It is a complex system that is learned and developed from childhood. The ability to rehabilitate such visual impairment is important to help traumatic brain injury patients recover and return to their normal lives.

Existing visual treatments primarily occur in office with the assistance of a visual therapist using traditional vision therapy (VT). Traditional vision therapy consists mainly of a progressive program of vision exercises, visual stimuli, or procedures conducted under the supervision of a therapist. Such treatment may be supplemented with in-home activities to be performed by the patient on his or her own.

DETAILED DESCRIPTION OF THE EMBODIMENTS

Embodiments of the disclosed technology generally include visual rehabilitation systems and methods that may be utilized in a provider's office or a patient's home.

The present invention focuses on the disruption of the magnocellular (ambient) processing, which affects their ability to concentrate on slower moving parvocellular (focal) processing signals and is more likely to be disturbed by the faster moving and now confusing external ambient signals. Brain trauma often causes a disruption in ambient processing and an inability to synchronize nonvisual subcortical signals with peripheral or central eyesight cortical signals.

This innovation promotes the healing and reorganization of a damaged visual system by appropriately stimulating the magnocellular (ambient) pathway. Neuroplasticity is the capacity of neurons and neural networks in the brain to change their connections and behavior in response to new information, sensory, stimulation, development, damage, or dysfunction. By appropriately stimulating the magnocellular system in isolation, we believe we can bring about improvement in that system because research has shown substantial changes can profoundly alter the pattern of neuronal activation in response to experience. The magnocellular pathway consists of larger neurons that are more reactive to lower contrasts. By using visual stimuli with precise contrast and frequency characteristics, the magnocellular (ambient) visual pathway may be isolated and rehabilitated through the use of the disclosed system and method.

Figure 1:
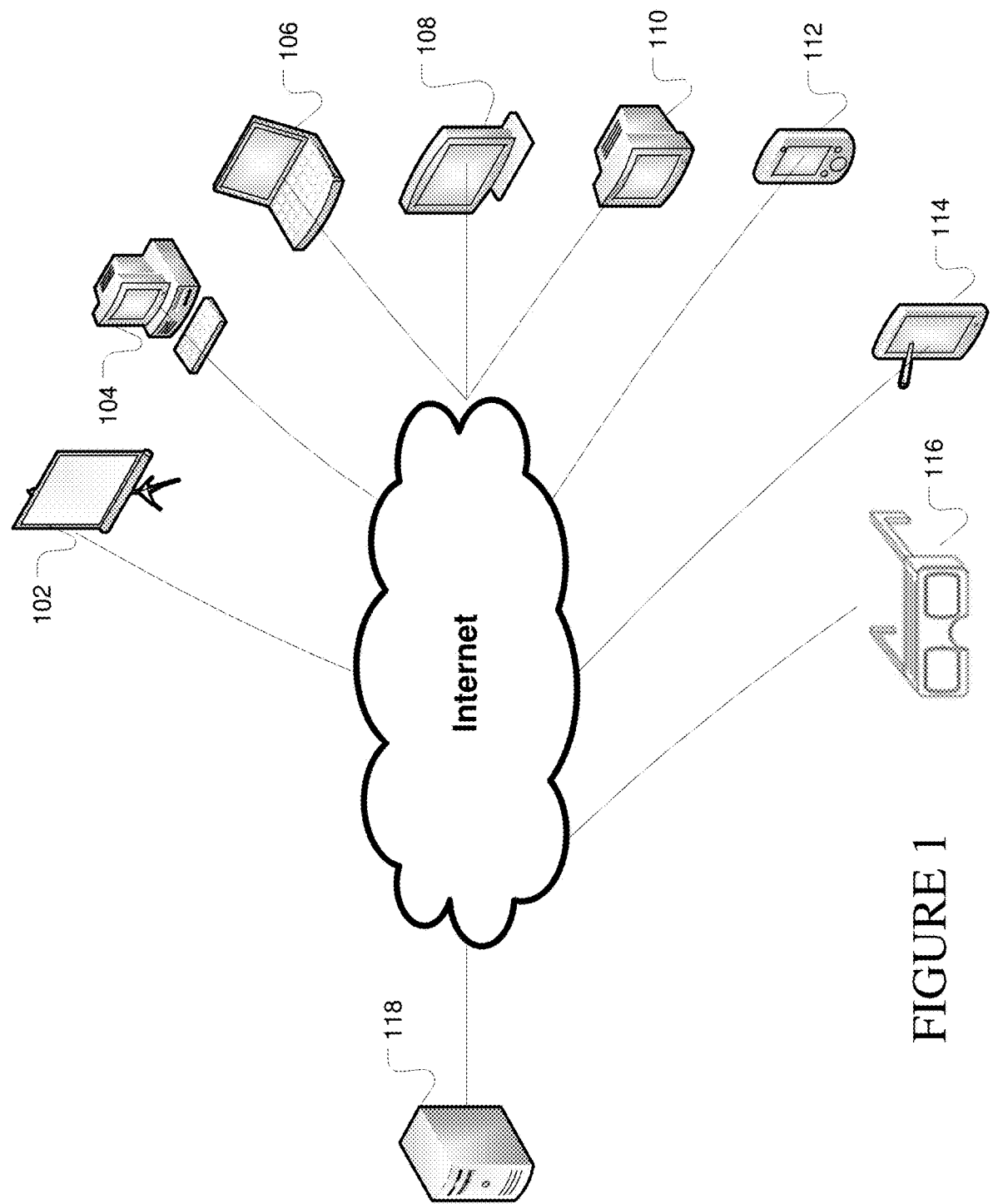
FIG. 1 shows embodiments of visual rehabilitation systems and methods.

FIG. 1 illustrates several possible embodiments for a user to implement the disclosed visual rehabilitation systems and methods. As will become apparent to one skilled in the art, the disclosed embodiments are merely exemplary in nature, and the systems and methods may be employed in any suitable environment. A number of different devices are available for a user to launch the visual rehabilitation program, such as desktop computer 104, laptop computer 106, cell phone 112, smart phone, other portable device, television 110, tablet 114, virtual reality goggles 116 (e.g., Google Cardboard™, Oculus Rift™, Samsung VR Gear™, Sony's Playstation VR®), projector screen 102, and other computing devices 108. It should be understood that these devices may be used in isolation or in any combination with other devices. For example, Google Cardboard™ may be used in combination with a smart phone.

Similarly, other portions of this discussion provided to aid in understanding the scope of the embodiments are not intended to, nor should be assumed to, limit the scope to the particular examples given. For example, the device discussed here is a portable device having a processor, network connection through a computer and/or on its own, etc. Many different types of devices may have these characteristics. As another example, the discussion here involves the visual rehabilitation program being implemented in a home setting, but may include different types of devices and may include other venues such as rehabilitation centers instead of a home setting.

As shown in the exemplary embodiment, a user may use any suitable internet access point, Wifi or ethernet, to access the visual rehabilitation system. In other embodiments, the user may use his or her service provider (e.g., AT&T, Verizon, T-mobile) to gain access to the visual rehabilitation program. The user may then optionally download the appropriate program to his or her device. Alternatively, the visual rehabilitation program may be streamed online and thus need not be downloaded to a local storage device. In other embodiments, possibly due to the traumatic brain injury, a user may be unable to operate the visual rehabilitation program without assistance. If this is the case, a visual rehabilitation therapist or a user's family member or friend may assist, download or initiate the program online for the user.

FIG. 1 shows an environment in which a user may download the visual rehabilitation program to be run on the user's device such as a desktop computer 104. The user may download the file from a server 118 controlled, for instance, by the user's visual therapist, whose patient-specific visual rehabilitation program may be available via the internet. In other embodiments, the visual rehabilitation program may be accessed by the user on his or her portable device via an application, which is downloadable to the user's device. Alternatively, a user may download the file while visiting the therapist's office or the program may be copied to some type of portable media, such as a recordable DVD or USB, for the user to take home.

Figure 2:
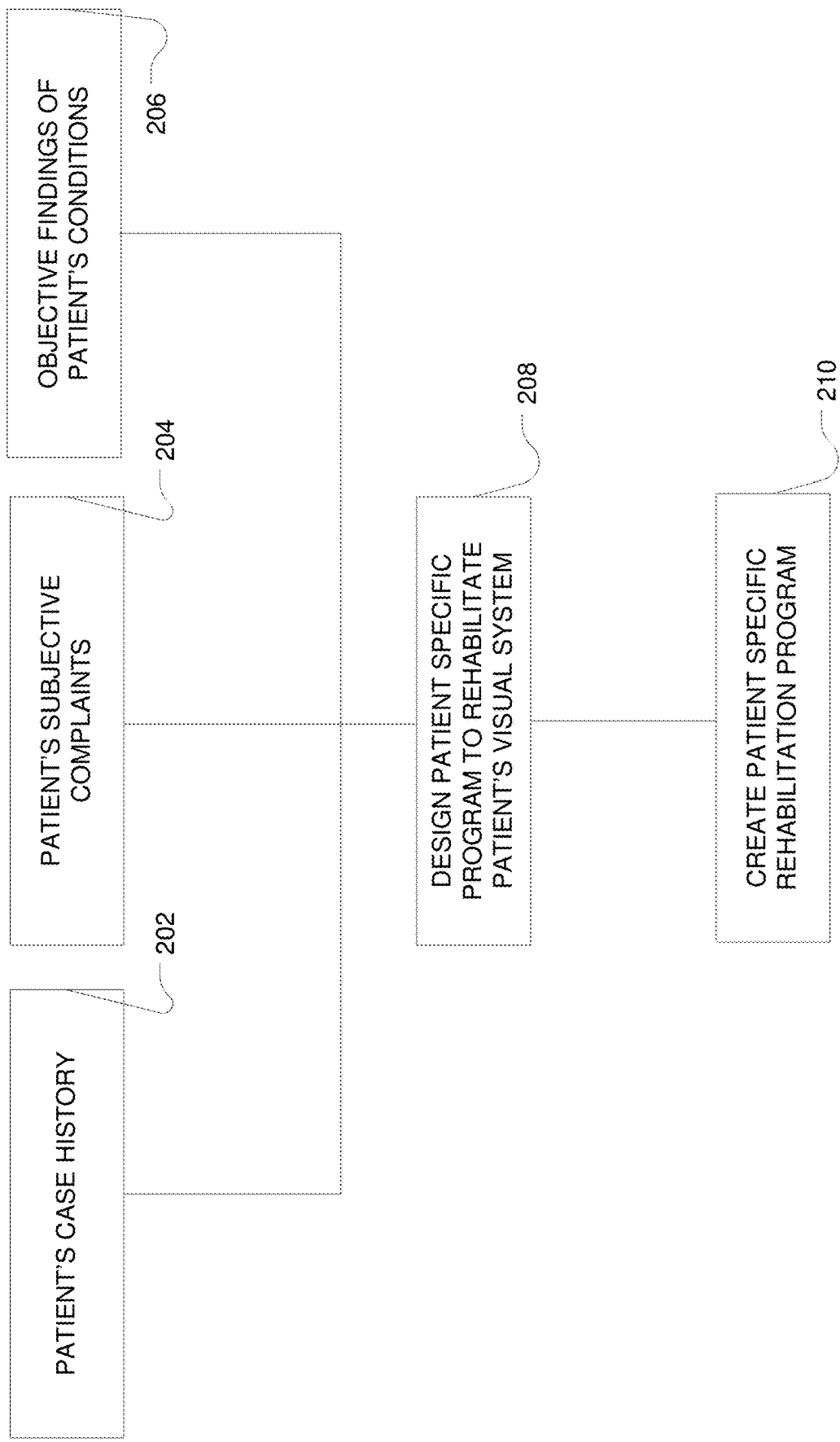
FIG. 2 shows a flow chart of an embodiment of a method to develop a visual rehabilitation program.

FIG. 2 demonstrates an exemplary embodiment of the implementation of the visual rehabilitation system. In the exemplary embodiment, a user may have an appointment with a doctor/therapist/rehabilitationist/analyst to analyze the patient's traumatic brain injury. One skilled in the art will appreciate that the disclosed persons, such as a therapist, are exemplary in nature and other individuals may be qualified to evaluate the user, design the system and/or method, and/or implement the system or method, such as a doctor. Further, the terms, user and patient, are used throughout the specification. While the terms, "user" and "patient," are used interchangeably throughout the specification, the user does not need to be formally diagnosed to qualify as a user of the system and/or method, as would be apparent to one skilled in the art. During the appointment between the user and the therapist, the user may be evaluated to develop a patient-specific visual rehabilitation program.

As shown in FIG. 2, the therapist may review the patient's case history at 202. The patient's case history may include how the patient incurred the brain injury, e.g., car accident, fall, combat injury, etc. The patient may further provide his or her own subjective complaints about his or her condition at 204. Finally, the therapist may observe and/or conduct tests on the user to obtain objective findings of the patient's condition at 206. The tests may vary widely from the simple to the complex, from a simple visual inspection of the patient to detailed MRI scans of the patient's brain. Such tests may be carried out, for example, by the doctor, doctor's assistant, radiologist or user at the instruction of the therapist. One test widely used in the evaluation of patients with traumatic brain injury is the Diopsys Nova-LX Visual Evoked Potential instrument.

It should be understood that the tests need not be conducted contemporaneously with the appointment but may have occurred previously and provided to the therapist at a later time. Further, one skilled in the art would understand that the therapist may use one, two, or all of the listed elements: the patient's case history 202, patient's subjective complaints 204, or objective findings of the patient's condition 206. Patient's conditions 206 may exemplarilary be but not limited to the following: dyslexia, post-traumatic stress disorder (PTSD), stroke, visual midline shift syndrome (VMSS) and/or physical trauma. Symptoms in the patient's case history may include but are not limited to spatial disorientation, impaired balance and posture, and poor visual memory and attention. Objective findings of the patient's conditions and symptoms may be obtained through a number of methods, including but not limited to visual evoked potential (VEP) and electroencephalogram (EEG). Once the patient's case history 202, patient's subjective complaints 204, and/or objective findings of the patient's conditions 206, the therapist may utilize some or all of this information to design a patient-specific rehabilitation program at 208. Optionally, in some embodiments, the therapist may present one or more images or stimulus to the patient and measure his or her reaction to the images prior to designing the final patient specific visual rehabilitation sequences. Once the therapist designs the patient specific visual rehabilitation sequences, the therapist creates the program at 210.

It should be further understood that the invention may develop visual rehabilitation programs for categories of patients. For example, after evaluating a patient's case history 202, patient's subjective complaints 204, and objective findings of the patient's conditions 206, and other relevant information, a therapist may categorize the patient into one of the previously-developed categories of patients. For purposes of illustration, there may be ten categories of patients based upon the severity of his or her traumatic brain injury and resulting visual impairments, from 1 (visual system only mildly impaired) to a 10 (visual system severely impaired). Once the patient is categorized based upon the severity of his or her injury, the therapist then begins treatment using the visual rehabilitation program for that category of patients.

Figure 3:
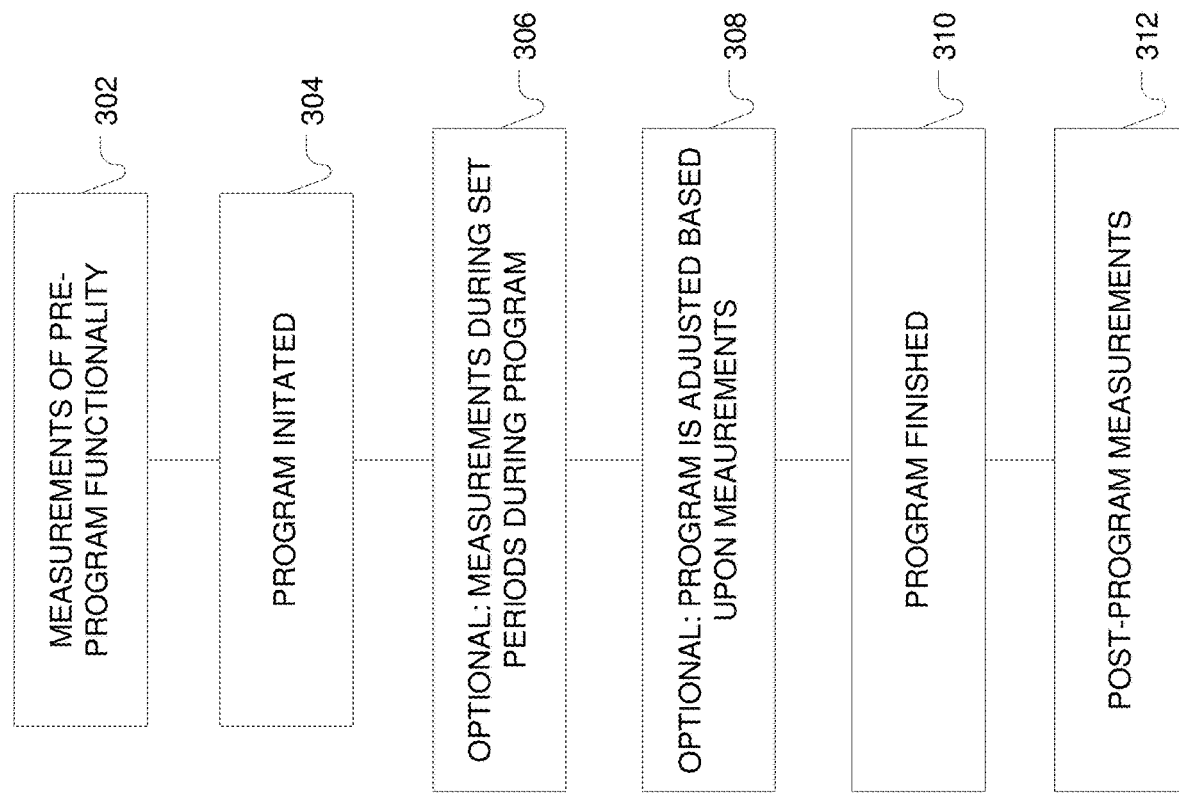
FIG. 3 shows a flow chart of an embodiment of a method for implementation of a visual rehabilitation program.

FIG. 3 demonstrates an exemplary embodiment of gathering measurements of a user's visual system. At 306, in one embodiment, the program may be paused at set intervals to review the user's measurements, e.g., ten minutes, twenty minutes, and thirty minutes. In other embodiments, the program may be paused at odd intervals to take measurements of the patient's visual system. These pauses may be made based upon the therapist's observations during testing. Such measurements may optionally be used to evaluate whether the program should be adjusted to more effectively rehabilitate the patient's visual system. At 308, the therapist may manually adjust the program to take into account the measurements taken during the program. In other embodiments, the program may automatically take into account the measurements taken during the pause and incorporate such measurements to adjust the visual rehabilitation program without the intervention of the therapist. In yet another embodiment, the program may be reinitiated without adjustment. The program ends at 310. Once the program ends, some or all of the measurements may then be used to measure the effectiveness of the patient's visual rehabilitation program, as shown at 312. As described in more detail below, measurements may also be taken in home by the user and sent to the therapist for review.

In certain embodiments, after the program has finished at 310, the therapist may then decide to adjust the program based upon some or all of the measurements taken before, during or after the program. Alternatively, the therapist may decide that the particular program is not effective for the patient in its entirety. If the therapist makes such a determination, the therapist may redesign the patient-specific rehabilitation program and/or recategorize the patient into a new patient category for previously-developed visual rehabilitation programs based upon patient class. The therapist may alternatively begin an entirely new rehabilitation program based upon said measurements.

Figure 4:
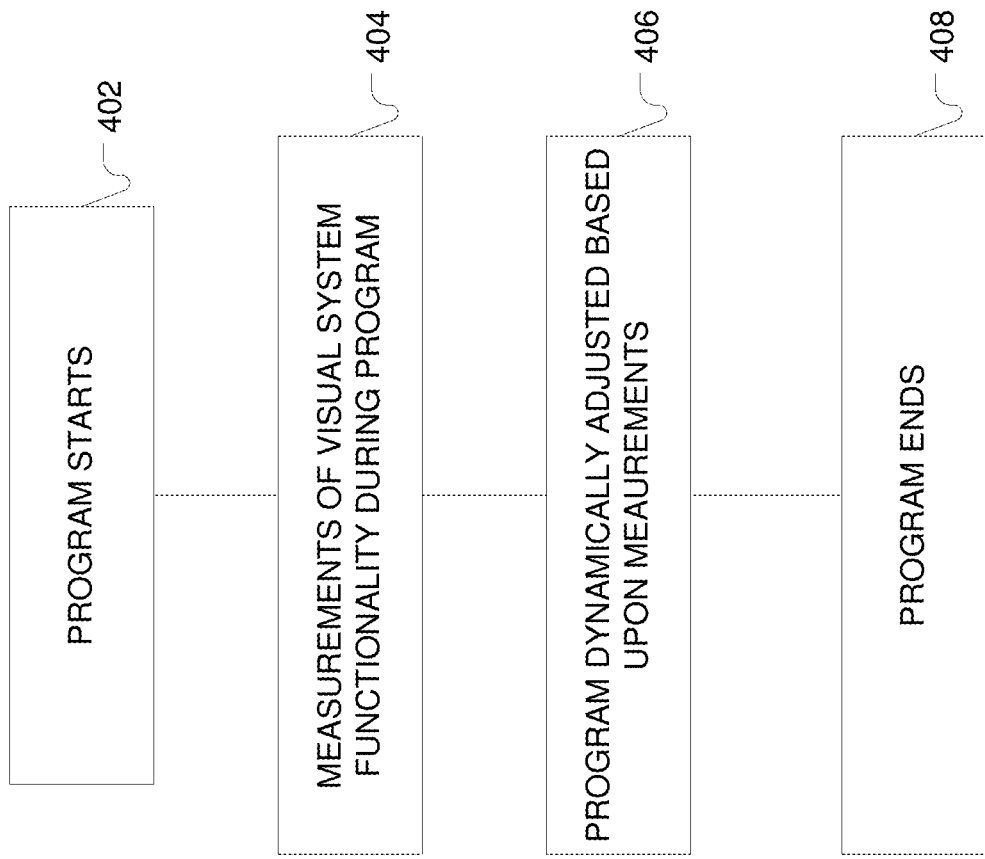
FIG. 4 shows a flow chart of an embodiment of a method for the implementation of a visual rehabilitation program.

FIG. 4 demonstrates an embodiment of the dynamic adjustment of the visual rehabilitation system and method. At 402, the user starts the program. For example, the user may be in an in-office setting with a therapist simultaneously measuring at 404 the patient's visual response to the program and dynamically adjusting the program in response to the measurements at 406. In other embodiments, the program may be adjusted automatically without intervention of the therapist, or alternatively, the therapist may view the measurement results and manually adjust the program based upon the measurements. In the in-office setting, the patient may use the program on a number of devices such as but not limited to a television, a laptop, a desktop computer, or virtual reality goggles (e.g., Oculus Rift Goggles™ or Google Cardboard™ with a smart phone). The program ends at 408.

In further embodiments, once the user has conducted a dynamic rehabilitation program session, a copy of the individualized program may be accessed over the internet or provided to the user to take home for in-home therapy. In other embodiments, the user may be given a similar or different individualized program to access or take for in-home therapy. The user may then use the program to rehabilitate on his or her own using his or her own device, such as a laptop, desktop computer or Google Cardboard™ with a smart phone. In some embodiments, the user may periodically visit the therapist's office to measure the effectiveness of the visual rehabilitation program. The frequency of such visits may vary widely, such as daily, weekly, monthly or annually.

During these visits, the therapist may test the effectiveness of the user's rehabilitation. The effectiveness of the rehabilitation may be evaluated in a number of manners. One embodiment is through the display of statistics to the therapist and may, optionally, be displayed to the user. Based upon the test results, the therapist may optionally adjust the individualized program. Such adjustments may be necessitated by the ineffectiveness of the program or whether the user's vision has improved/digressed and requires adjustments of the program to take into account the user's progression/digression.

Figure 5:
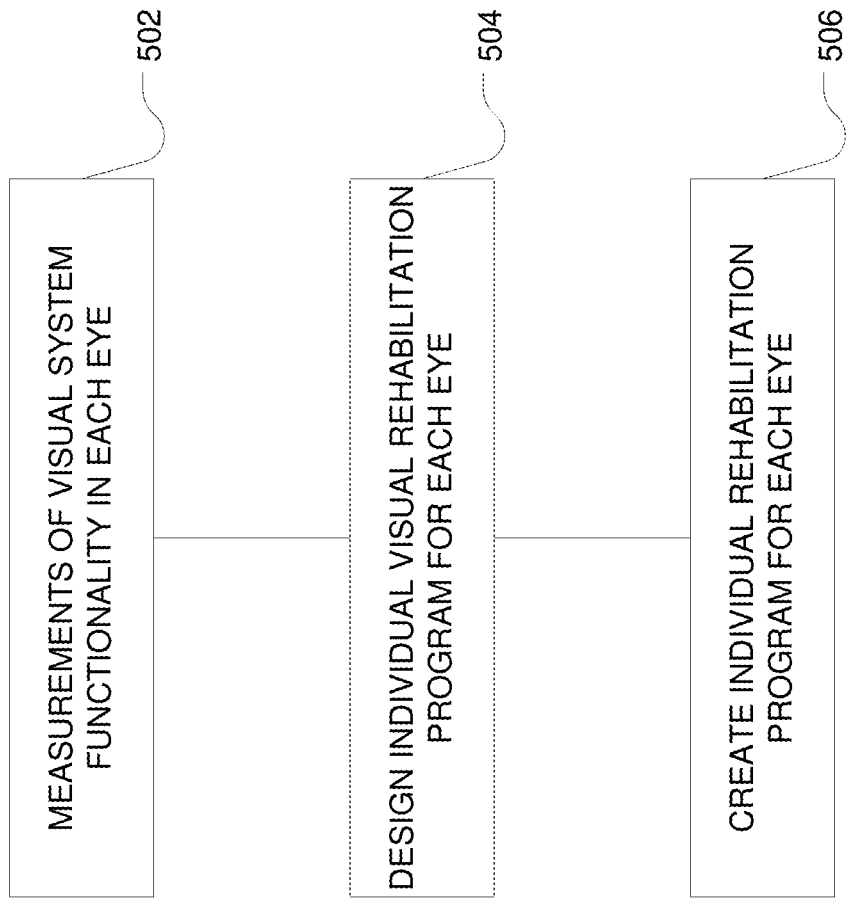
FIG. 5 shows a flow chart of an embodiment of a method for development of a visual rehabilitation program for each individual eye.

FIG. 5 demonstrates an exemplary embodiment of individual visual rehabilitation programs for each eye of the user. Rather than developing one program for the user to implement for both eyes, the visual rehabilitation program may be individualized to each eye. For example, the user's vision may be more significantly impacted in the right eye, whereas the left eye does not suffer from the same degree of visual deficiencies. The invention permits the therapist to design a more intense visual rehabilitation program for the right eye and a different program for the right eye. As is described in more detail below, an eye-specific rehabilitation program may be implemented via virtual reality goggles, which a user may either use in-office or at home. In a different embodiment, the user may be instructed to cover the left eye while viewing the portion of the program for the right eye. The user may then switch the eye cover to the right eye while viewing the left eye visual rehabilitation program.

As shown in FIG. 5, the therapist may obtain measurements of the visual system in each eye at 502. Based upon these measurements, the therapist takes into account differences between each eye when designing the visual rehabilitation system. If each eye has the same level of impairment, then the therapist may design one program to use in both eyes. However, as shown in the embodiment found in FIG. 5, each eye may have different levels of damage and need to rehabilitate using different methods and/or different paces. The therapist thus designs at 504 and creates at 506 two different rehabilitation programs. The user may then rehabilitate in the office or take both programs home.

Figure 6:
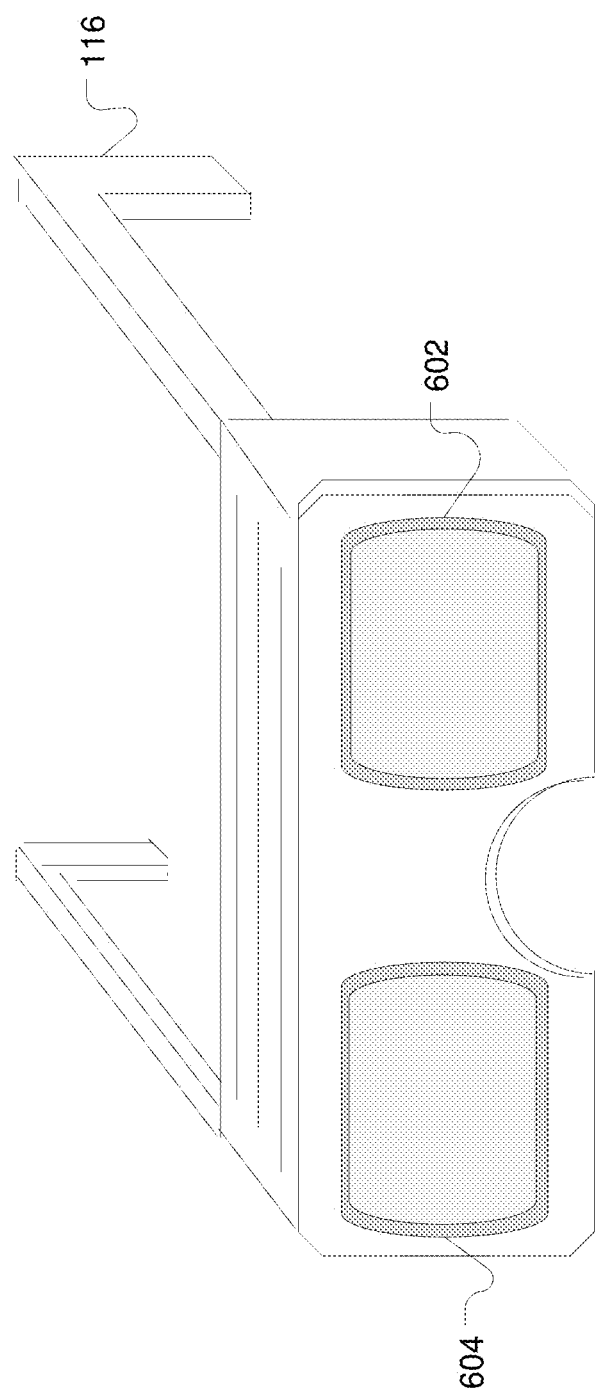
FIG. 6 shows an exemplary embodiment for a user to implement the disclosed visual rehabilitation systems and methods.

FIG. 6 illustrates an exemplary embodiment, virtual reality goggles 116, for a user to implement the disclosed visual rehabilitation system and methods, particularly when the rehabilitation program has been individualized for each eye. If the same visual rehabilitation program is being used in both eyes, then the program can play in both virtual reality goggle lenses 602 and 604. In other embodiments, the user may have two visual rehabilitation programs, one for each eye. The program for the user's left eye may play in the left lens at 602, and the right lens 604 of the virtual reality goggles may play the rehabilitation program for the right eye. The two programs may play simultaneously in both lenses 602 and 604. Alternatively, the two rehabilitation programs may play at separate times. For example, the right eye rehabilitation program may play for the user, followed immediately by the rehabilitation program for the left eye. In other embodiments, there may be a pause of varying periods between the user viewing each program. For example, the user may have a rest period of seconds, minutes, hours, days, or weeks, depending on his or her rehabilitation program.

Figure 7:
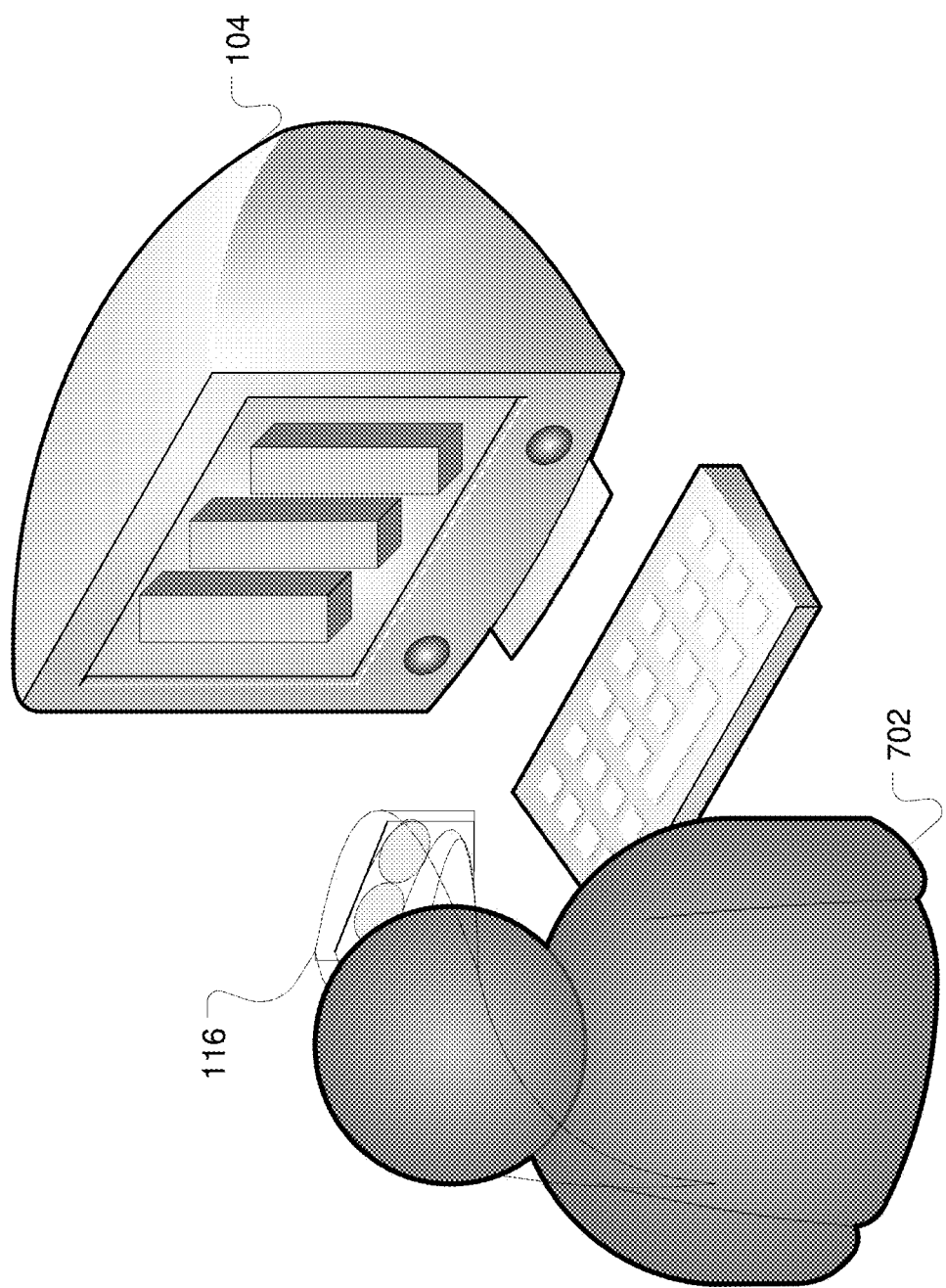
FIG. 7 shows an exemplary embodiment in which a user is conducting an in-home visual rehabilitation program.

FIG. 7 illustrates an exemplary embodiment in which a user 702 is conducting an in-home visual rehabilitation program using virtual reality goggles 116 and a desktop computer 104. Other types of equipment may be used other than those shown in FIG. 7. Further, any or all of the listed or illustrative equipment may be used individually or in combination. The visual rehabilitation program may be provided to the user via a computer readable medium, such as the internet, hard copy, or through some other means.

In the example, the visual rehabilitation program may exemplarily run on the user's computer and guide the user through the use of the virtual reality goggles to run the rehabilitation program for each eye. For example, the program may instruct the user to place the virtual reality goggles on his or her head. Once placed, the program may audibly, visually, or by some other method, such as vibration, prompt that the user to indicate when he or she is ready to begin the program. In other embodiments, the visual rehabilitation program may start after a set period of time, such as one minute after the instruction program is opened on his or her desktop computer 104. In some embodiments, once the program begins, the visual rehabilitation program may automatically play and stop in one or both lens of the virtual reality goggles 116. In yet other embodiments, the user may be instructed to trigger and/or end the program by selecting keys on his or her desktop computer 104. The user may also have the ability to pause the visual rehabilitation program for any reason or only a select number of reasons.

Following a visual rehabilitation program session, the user may, in certain embodiments, complete some questions and/or tests to measure the effectiveness of the visual rehabilitation program. Through the method, the visual rehabilitation program may communicate through some medium, such as the internet, to the therapist as to the user's progression and/or digression. Based upon the measurements sent to the therapist, the therapist may adjust the visual rehabilitation program over the internet, thus allowing the user to initiate an updated visual rehabilitation program without visiting the therapist's office. In yet other embodiments, the user may communicate with his or her therapist through the program to ask questions or make comments regarding the visual rehabilitation program.

Further, the virtual reality goggles 116 or some other type of equipment may enable a user to take his or her self-measurements at home. Such exemplary equipment may include a scoring program provided by the therapist to the user. By taking measurements at home, the user may not need to visit the therapist as frequently as if he or she did not have said measuring equipment at home. Such measurements enable the user to report his or her improvement or regression to the therapist without visiting the office.

Figure 8:
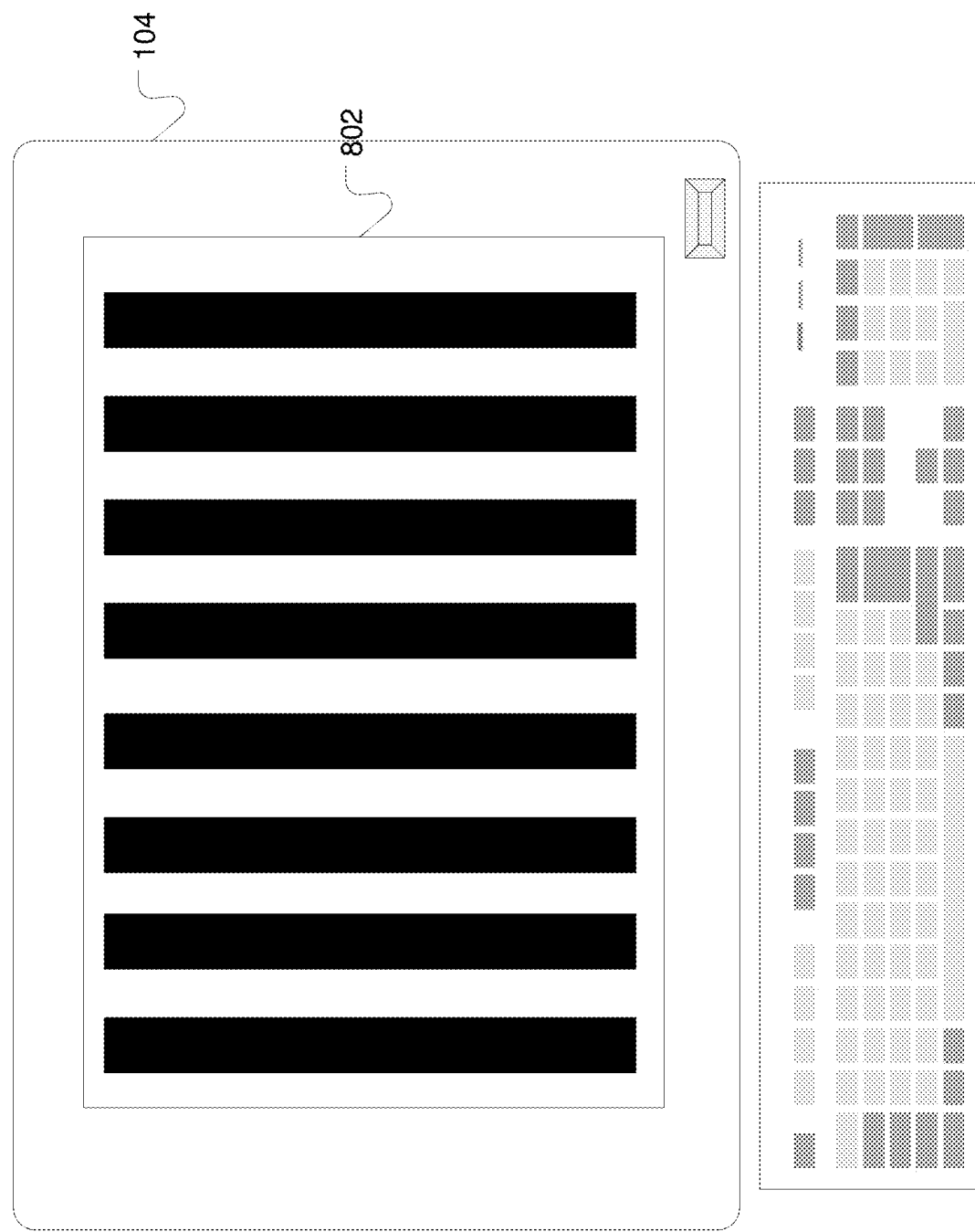
FIG. 8 shows an exemplary embodiment of a portion of a visual rehabilitation program.

FIG. 8 illustrates an exemplary embodiment of a portion of a visual rehabilitation program. An image 802 may be displayed to the user on, for example, a desktop 104. The edges of said images may be hard or blended. Further embodiments of the images may change geometric size and animation speed. The images may be static, dynamic, animated, move horizontally, move vertically, fade away, and/or fade into view.

The images may be 2-dimensional (2-D) or 3-dimensional (3-D). In one embodiment, a patient may begin with 2-D images and progress to 3-D images. The images may further include in some embodiments a virtual life-like scenario, such as a patient practicing entering a moving escalator.

Varying time periods may be used when displaying the image to the user, such as milliseconds, seconds, minutes, or other varying lengths of time depending on the rehabilitation protocol for the user. In some embodiments, the image displays less than 10 milliseconds. In other embodiments, the images are shown for 90 seconds at a time.

A number of images may be used in the visual rehabilitation program. Such images include, but are not limited to, the following of varying size, shape, color, contrast, blending; warping: (1) checkerboards; (2) horizontal stripes; (3) vertical stripes; (4) horizontal sinusoidal stripes; (5) vertical sinusoidal stripes; (6) tree trunks; and/or (7) shapes, such as a bird, circle, square, fish. Other exemplary images, but are not limited to, the following of varying size, shape, color, contrast, blending; warping: (1) checkerboards; (2) horizontal stripes; (3) vertical stripes; (4) horizontal sinusoidal stripes; (5) vertical sinusoidal stripes; (6) tree trunks; (7) shapes, such as a bird, circle, square, fish; and/or (8) bouncing balls. In other embodiments, the images incorporate real-life or life-like interactive objects, such as but not limited to manipulating coins, placing puzzle pieces, and entering escalators. Further, in an exemplary embodiment, the background of the image will remain stationary while the object dynamically moves, such as a moving escalator.

It should be understood that these images may be displayed in isolation or in any combination with other images. The images displayed in each visual rehabilitation program may range from one to twenty, for example. In one exemplary embodiment, the visual rehabilitation program is comprised of three images. The images may be shown simultaneously or in quick succession. In other embodiments, the visual rehabilitation program is a series of the above images shown in succession with a pause between the images.

Figure 9:
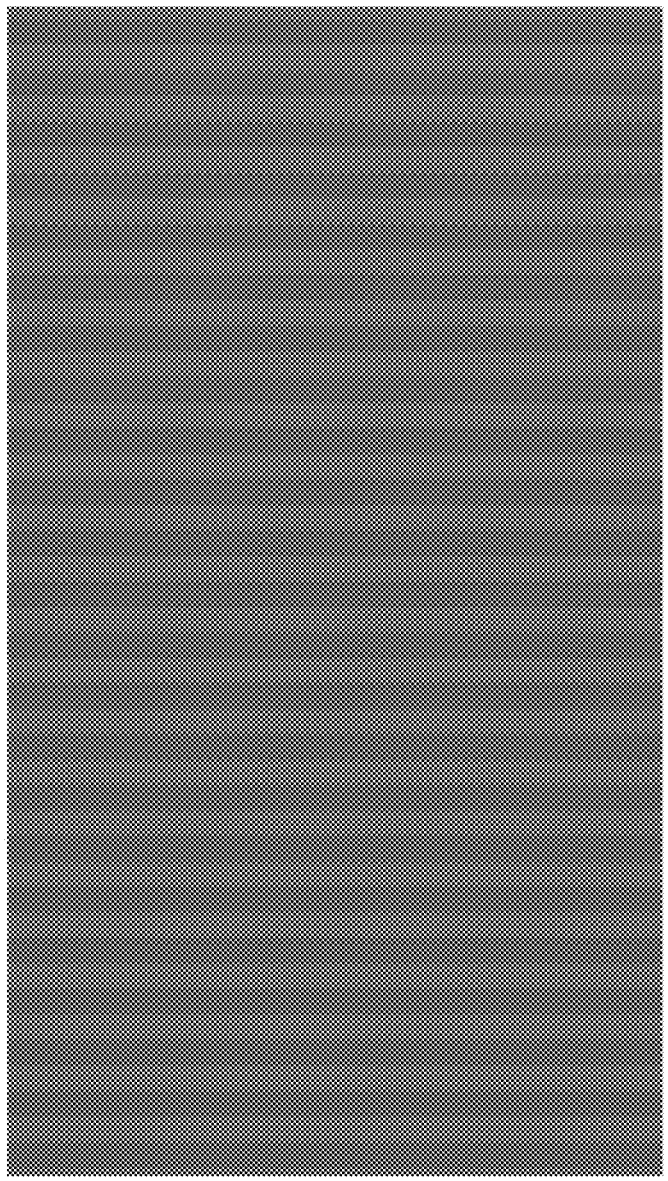
FIG. 9 shows a first exemplary embodiment that may be used in a visual rehabilitation program.

FIG. 9 shows a first exemplary embodiment that may be used in a visual rehabilitation program. The exemplary image shown in FIG. 9 is vertical stripes. Such stripes may vary in size, contrast, color, shade, speed, movement, consistency, fading, width, length, and frequency. The image may further be static or dynamic.

Figure 10:
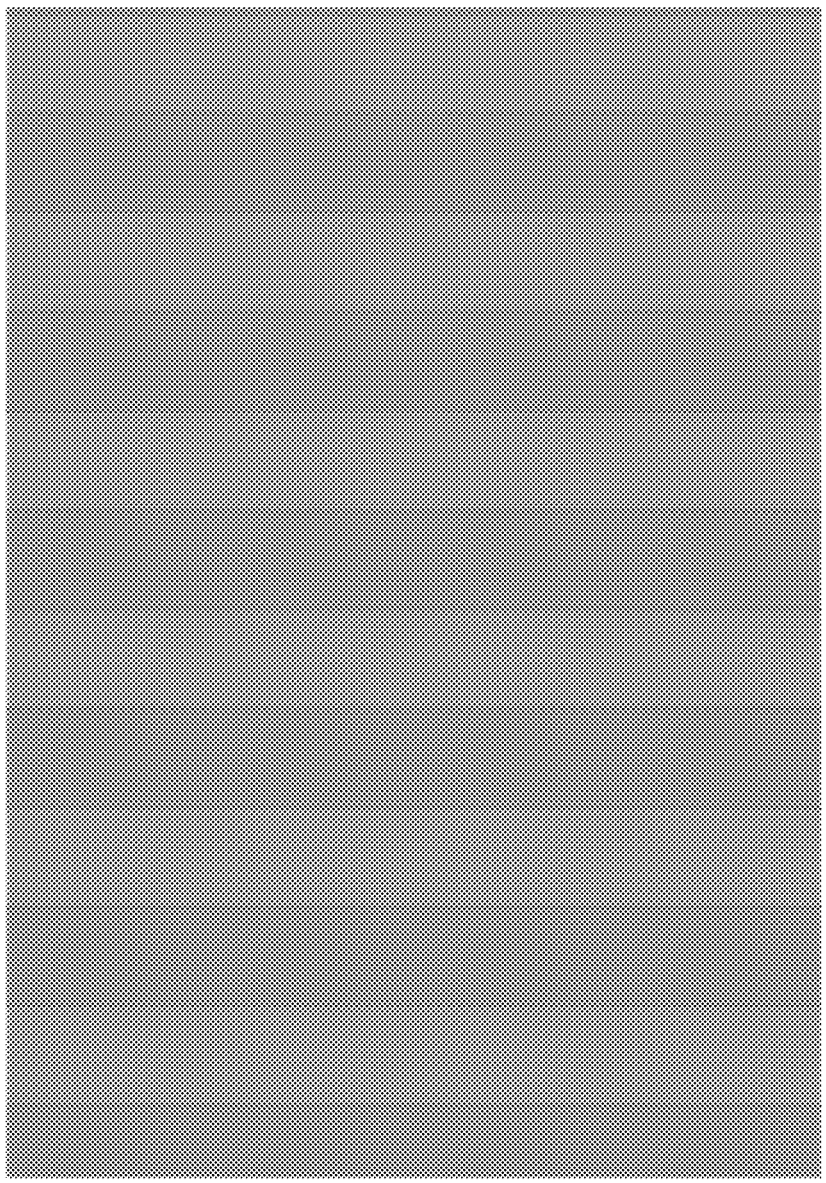
FIG. 10 shows a second exemplary embodiment that may be used in a visual rehabilitation program.

FIG. 10 shows a second exemplary embodiment that may be used in a visual rehabilitation program. The exemplary image shown in FIG. 10 is vertical stripes. Such stripes may vary in size, contrast, color, shade, speed, movement, consistency, fading, width, length, and frequency. The image may further be static or dynamic.

Figure 11:
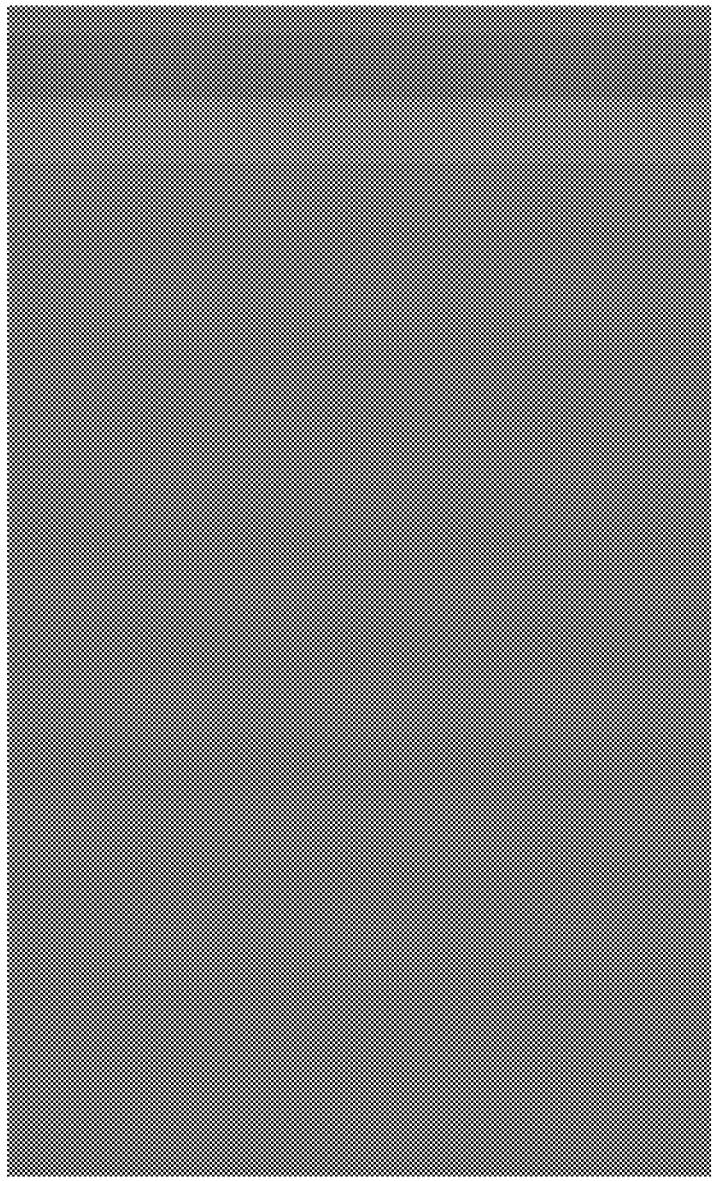
FIG. 11 shows a third exemplary embodiment that may be used in a visual rehabilitation program.

FIG. 11 shows a third exemplary embodiment that may be used in a visual rehabilitation program. The exemplary image shown in FIG. 11 is vertical stripes. Such stripes may vary in size, contrast, color, shade, speed, movement, consistency, fading, width, length, and frequency. The image may further be static or dynamic.

Figure 12:
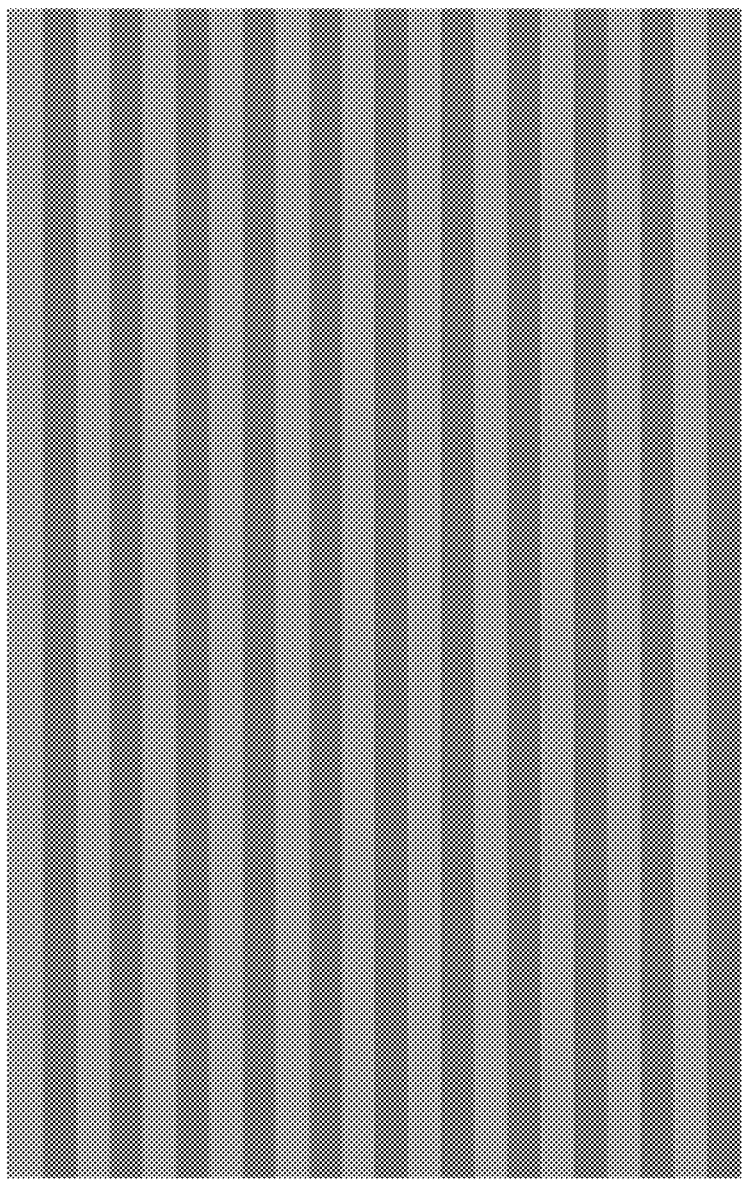
FIG. 12 shows a fourth exemplary embodiment that may be used in a visual rehabilitation program.

FIG. 12 shows a fourth exemplary embodiment that may be used in a visual rehabilitation program. The exemplary image shown in FIG. 12 is horizontal stripes. Such stripes may vary in size, contrast, color, shade, speed, movement, consistency, fading, width, length, and frequency. The image may further be static or dynamic.

Figure 13:
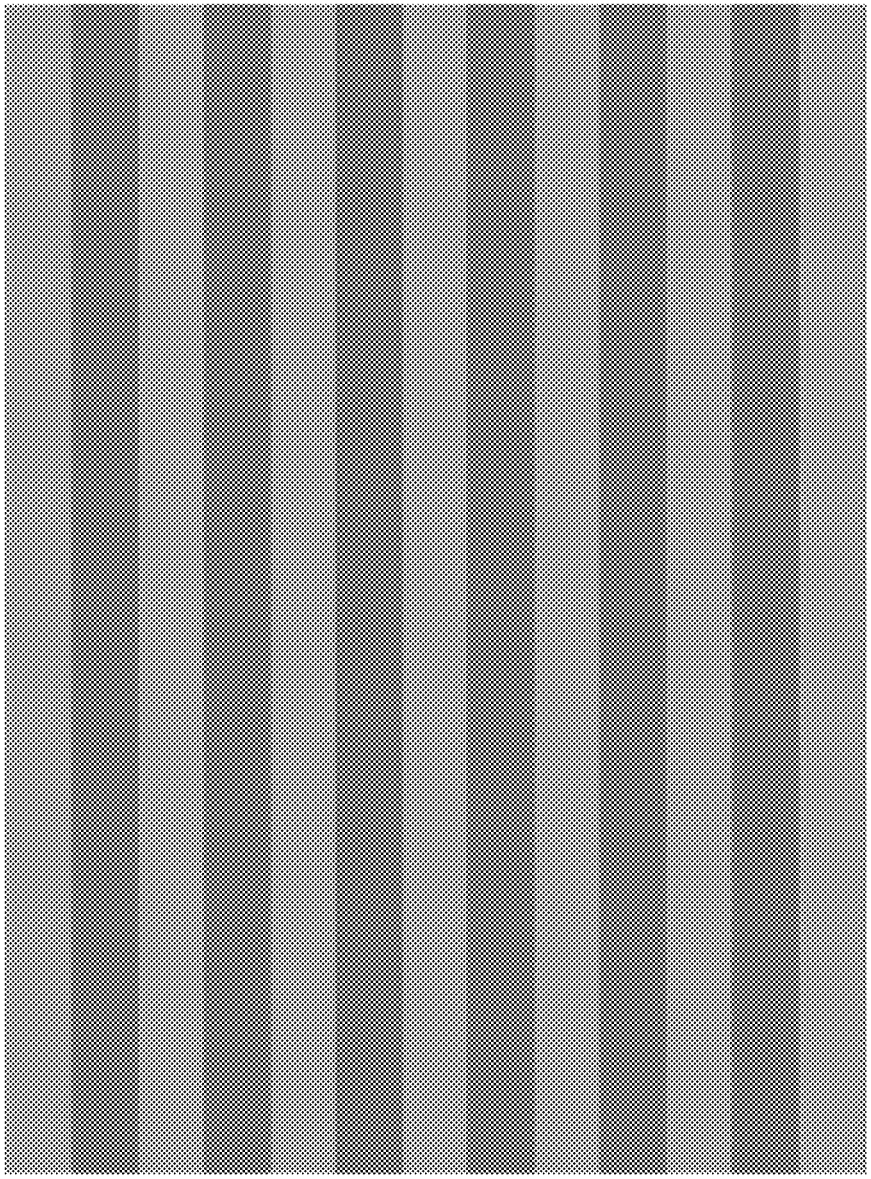
FIG. 13 shows a fifth exemplary embodiment that may be used in a visual rehabilitation program.

FIG. 13 shows a fifth exemplary embodiment that may be used in a visual rehabilitation program. The exemplary image shown in FIG. 13 is horizontal stripes. Such stripes may vary in size, contrast, color, shade, speed, movement, consistency, fading, width, length, and frequency. The image may further be static or dynamic.

Figure 14:
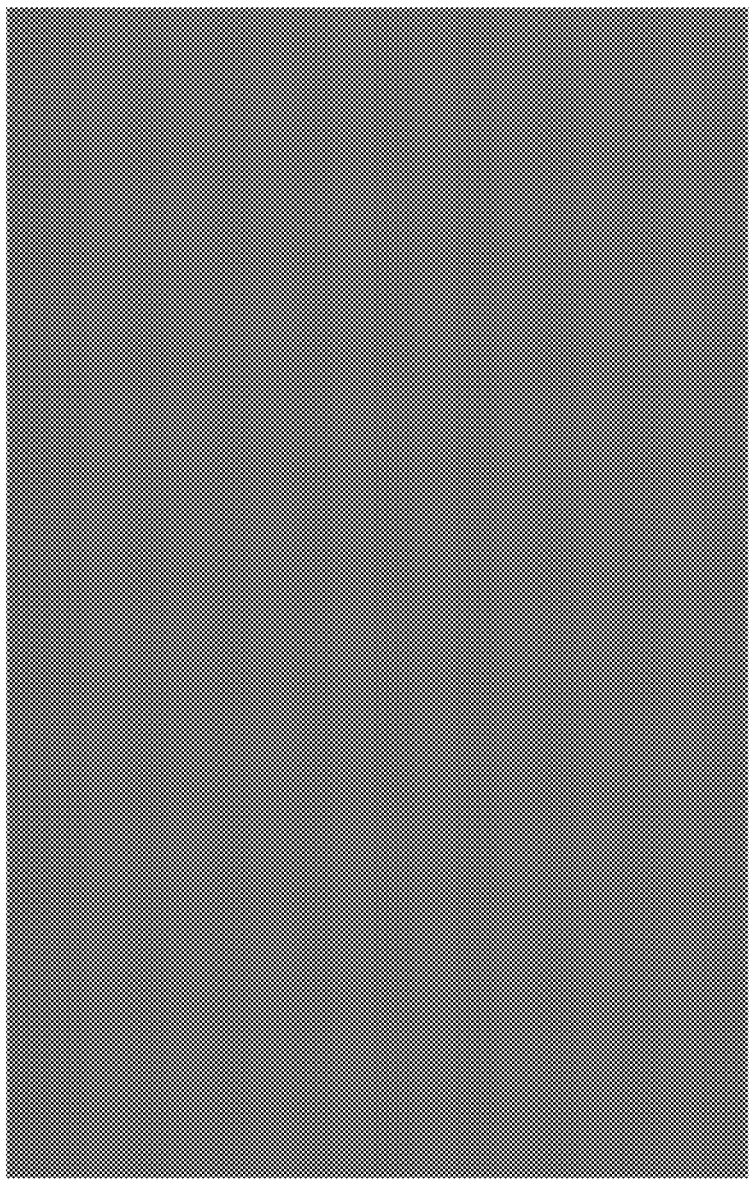
FIG. 14 shows a sixth exemplary embodiment that may be used in a visual rehabilitation program.

FIG. 14 shows a sixth exemplary embodiment that may be used in a visual rehabilitation program. The exemplary image shown in FIG. 14 is horizontal stripes. Such stripes may vary in size, contrast, color, shade, speed, movement, consistency, fading, width, length, and frequency. The image may further be static or dynamic.

Figure 15:
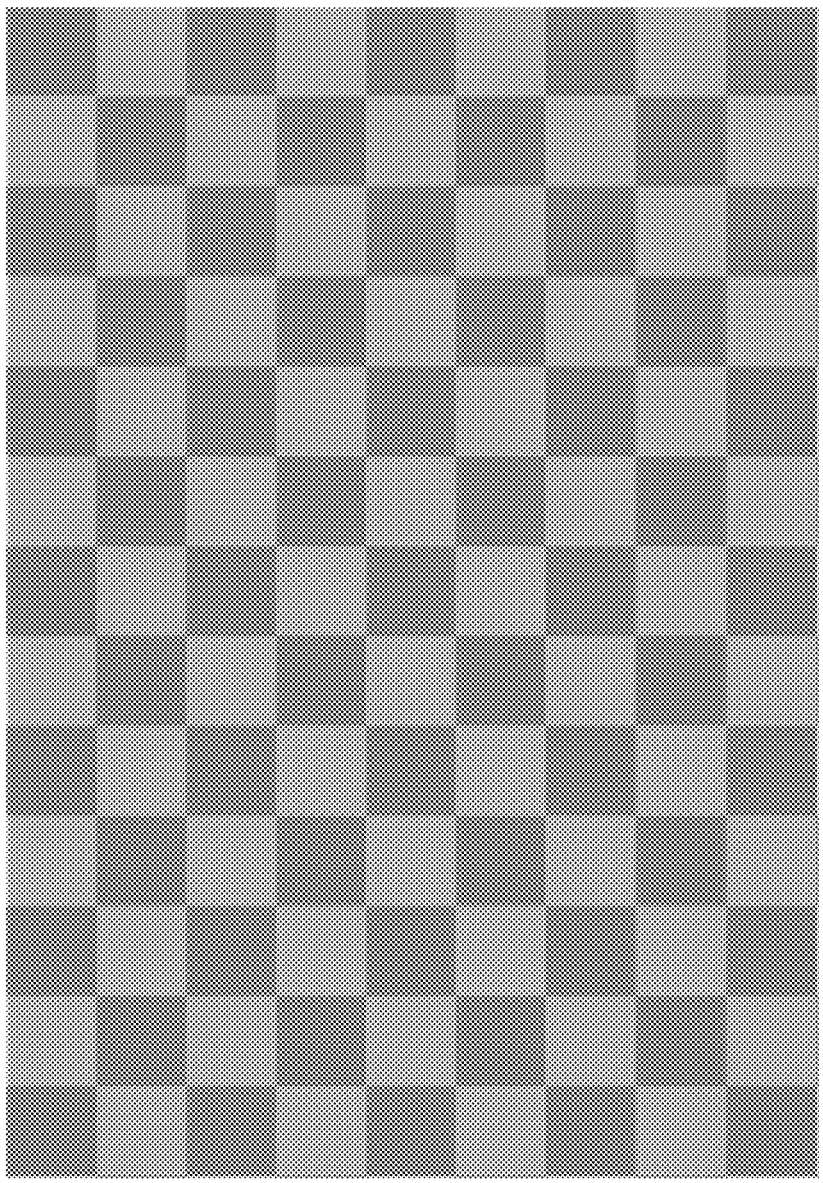
FIG. 15 shows a seventh exemplary embodiment that may be used in a visual rehabilitation program.

FIG. 15 shows a seventh exemplary embodiment that may be used in a visual rehabilitation program. The exemplary image shown in FIG. 15 is a checkerboard. Such stripes may vary in size, contrast, color, shade, speed, movement, consistency, fading, width, length, and frequency. The image may further be static or dynamic.

Figure 16:
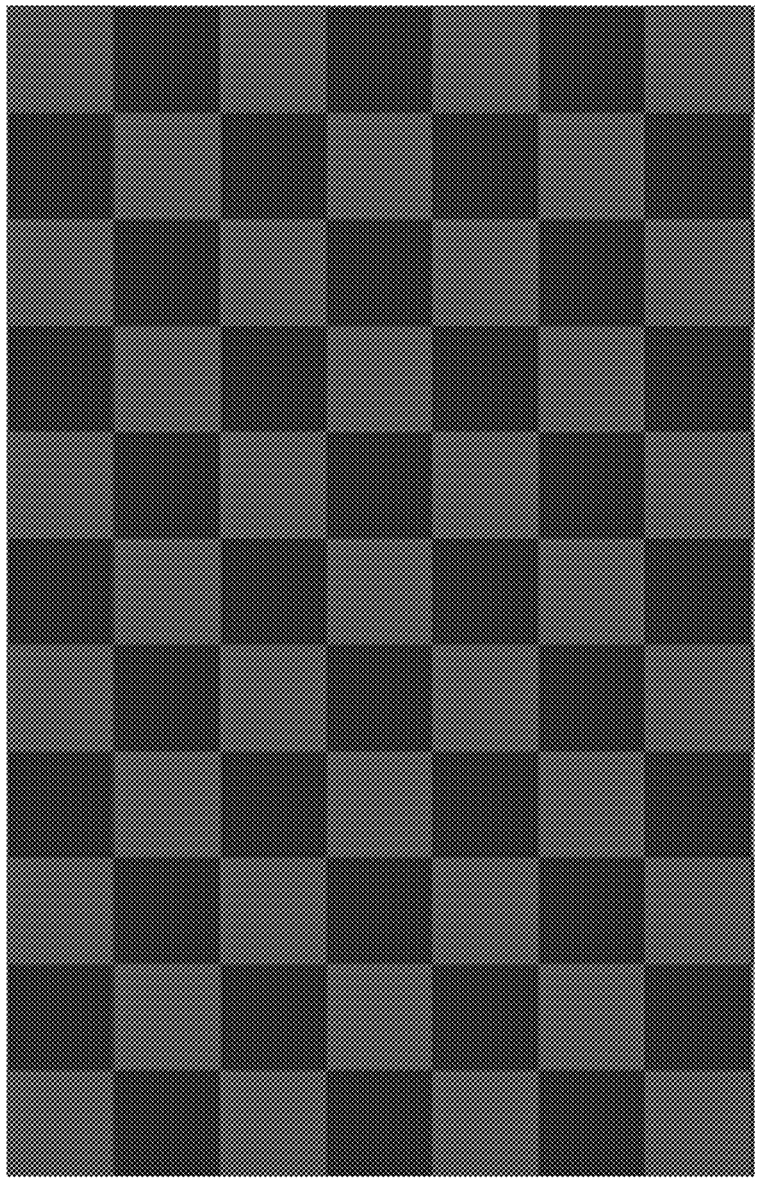
FIG. 16 shows an eighth exemplary embodiment that may be used in a visual rehabilitation program.

FIG. 16 shows an eighth exemplary embodiment that may be used in a visual rehabilitation program. The exemplary image shown in FIG. 16 is a checkerboard. Such stripes may vary in size, contrast, color, shade, speed, movement, consistency, fading, width, length, and frequency. The image may further be static or dynamic.

The images may contrast and have varying frequencies. For example, the stimuli contrast may vary between one-half percent (0.5%) and twenty (20%) percent contrast with varying frequencies, degrees of complexity, animation, and user interaction. In another embodiment, the stimuli contrast is 15%. In some embodiments, the variety of contrast increases in complexity as the visual rehabilitation program progresses. Frequencies may vary from 0.5 hertz and up. These numbers are exemplary and not intended as a limitation.

Further, the user may interact with the images or the images may play independent of user interaction. If the images are interactive, successive images may vary dependent on user interaction. For example, in one embodiment, a user may indicate to the program when an image, such as a circle, has become visible. Based upon the user's response, a new image, such as horizontal stripes, may appear to the user. If the user fails to interact with the initial image, the new image may not be displayed to the user. Rather, the visual rehabilitation program may continue to display variations of the same image until the user's visual system has progressed to the necessary level to progress to the next image.

The above descriptions are merely some examples of capabilities available with the ability to use the visual rehabilitation system and/or method. No limitation to any particular embodiment is intended nor should be implied. Different processes and components of the various processes may be separated and/or combined differently within the scope of embodiments.

It will be appreciated that several of the above-disclosed and other features and functions, or alternatives thereof, may be desirably combined into many other different systems or applications. Also that various presently unforeseen or unanticipated alternatives, modifications, variations, or improvements therein may be subsequently made by those skilled in the art which are also intended to be encompassed by the embodiments here.

The invention claimed is:

1. A visual rehabilitation system, comprising:
  a virtual reality (VR) device;
  a processor; and
  a computer readable medium having computer-executable instructions comprising at least one visual rehabilitation program that, when executed by the processor, cause the processor to perform a visual rehabilitation method including causing the VR device to stimulate a magnocellular pathway of a user in isolation by visually presenting to the user one or more images, wherein the one or more of images are selected from a group consisting of the following: checkerboards, horizontal stripes, vertical stripes, horizontal sinusoidal stripes, and vertical sinusoidal stripes.

2. The visual rehabilitation system of claim 1, wherein the VR device has two lenses.

3. The visual rehabilitation system of claim 2, wherein the visual rehabilitation method includes the VR device visually presenting the one or more images by way of each of the two lenses.

4. The visual rehabilitation system of claim 2, wherein the at least one visual rehabilitation program includes a first rehabilitation program that is individualized for a first eye of the user and a second rehabilitation program that is individualized for a second eye of the user.

5. The visual rehabilitation system of claim 4, wherein the first visual rehabilitation method includes the VR device visually presenting at least one of the one or more images to the first eye by way of a first one of the two lenses.

6. The visual rehabilitation system of claim 5, wherein the second visual rehabilitation method includes the VR device visually presenting at least one of the one or more images to the second eye by way of a second one of the two lenses.

7. The visual rehabilitation system of claim 6, wherein the first and second visual rehabilitation methods are performed simultaneously.

8. The visual rehabilitation system of claim 6, wherein the first and second visual rehabilitation methods are performed at separate times.

9. The visual rehabilitation system of claim 8, wherein there is a pause between the first and second visual rehabilitation methods.

10. The visual rehabilitation system of claim 9, wherein the pause includes a rest period having a duration of one of the following: seconds, minutes, hours, days, and weeks.

11. The visual rehabilitation system of claim 1, wherein the one or more images are shown in succession.

12. The visual rehabilitation system of claim 1, wherein the one or more images are shown simultaneously.

13. The visual rehabilitation system of claim 1, wherein the visual rehabilitation method is self-administered.

14. The visual rehabilitation system of claim 1, wherein the visual rehabilitation method is performed in a home setting.

15. The visual rehabilitation system of claim 1, wherein the visual rehabilitation method is customized to the user.

16. The visual rehabilitation system of claim 1, wherein the visual rehabilitation method is developed based on at least one selected from a group consisting of the following: the user's symptoms, an objective evaluation of the user's condition, the user's subjective complaints, the user's conditions, and the user's history.

17. The visual rehabilitation system of claim 1, wherein the one or more images are either or both static and dynamic.

18. A visual rehabilitation system, comprising:
  a virtual reality (VR) device;
  a processor; and
  a computer readable medium having computer-executable instructions comprising at least one visual rehabilitation program that, when executed by the processor, cause the processor to perform a visual rehabilitation method including causing the VR device to stimulate a magnocellular pathway of a user in isolation by visually presenting to the user one or more images, wherein the visual rehabilitation method includes causing the VR device to visually present to the user the one or more images for less than 10 milliseconds.

19. A visual rehabilitation system, comprising:
  a virtual reality (VR) device;
  a processor; and
  a computer readable medium having computer-executable instructions comprising at least one visual rehabilitation program that, when executed by the processor, cause the processor to perform a visual rehabilitation method including causing the VR device to stimulate a magnocellular pathway of a user in isolation by visually presenting to the user one or more images, wherein the visual rehabilitation method includes causing the VR device to visually present to the user the one or more images for at least 90 seconds.

* * * * *